US005821235A

United States Patent [19]
Henning et al.

[11] Patent Number: 5,821,235
[45] Date of Patent: Oct. 13, 1998

[54] GENE THERAPY USING THE INTESTINE

[75] Inventors: Susan June Henning; Fred D. Ledley, both of Houston, Tex.

[73] Assignee: Baylor College of Medicine, Houston, Tex.

[21] Appl. No.: 376,473

[22] Filed: Jan. 20, 1995

Related U.S. Application Data

[63] Continuation of Ser. No. 862,882, Apr. 3, 1992, abandoned.
[51] Int. Cl.$^6$ ........................... A01N 43/04; A61K 31/70; A61M 5/14; C12N 15/09
[52] U.S. Cl. ........................... 514/44; 435/69.1; 435/70.3; 435/172.3; 435/320.1; 604/264; 604/265; 604/266; 424/93.21
[58] Field of Search ............................... 435/69.1, 240.1, 435/240.2, 240.21, 320.1, 172.1, 172.3, 70.3; 514/44; 128/4, 8, 772; 604/51, 264, 265, 266; 424/93.21

[56] References Cited

U.S. PATENT DOCUMENTS

| | | | |
|---|---|---|---|
| 4,637,814 | 1/1987 | Leiboff | 604/27 |
| 4,920,209 | 4/1990 | Davis et al. | 435/235.1 |
| 5,073,166 | 12/1991 | Parks et al. | 604/93 |
| 5,240,846 | 8/1993 | Collins et al. | 435/240.1 |

OTHER PUBLICATIONS

Vander et al., "Human Physiology: The Mechanisms of Body Function", (1970) McGraw–Hill (N.Y.), pp. 31–60, 355–390.
Vennes, Cecil–Textbook of Medicine, 18th edition, vol. 1 (1988), Wyngaarden and Smith Ed., W.B. Saunders Co. (Philadelphia), pp. 669–674.
Sweetser et al., "Transgenic Mice Containing Intestinal Fatty Acid–Binding Protein–Human Growth Hormone Fusion Genes Exhibit Correct Regional and Cell–Specific Expression of the Reporter Gene in Their Small Intestine", 85 *Proc. Natl. Acad. Sci. USA* 9611 (1988).
Leeper and Henning, "Development and Tissue Distribution of Sucrase–Isomaltase mRNA in Rats", 258 *American Journal of Physiology* G52 (1990).
Hansbrough et al., "Expression of a Liver Fatty Acid Binding Protein/Human Decay Accelerating Factor/HLA–B44 Chimeric Gene in Transgenic Mice", 260 *American Journal of Physiology* G669 (1991).
Chastre et al., "Functional Insertion of the SV40 Large T Oncogene in Cystic Fibrosis Intestinal Epithelium", 266 *J. Biol. Chem.* 21239 (1991).
Jones et al., "Ectopic Correction of Ornithine Transcarbamylase Deficiency in Sparse Fur Mice", 265 *J. Biol. Chem.* 14684 (1990).
Duch et al., "Biopterin Cofactor Biosynthesis: GTP Cyclohydrolase, Neopterin and Biopterin in Tissues and Body Fluids of Mammalian Species", 35 *Life Sciences* 1895 (1984).
Chowdhury et al., "Long–Term Improvement of Hypercholesterolemia After Ex Vivo Gene Therapy in LDLR–Deficient Rabbits", 254 *Science* 1802 (1991).
Sorlano–Brocher et al., "Gene Transfer into the Intestinal Epithelium", Abstract, *Gastroenterology* vol. 100 (1991).
Lau et al., "The Intestine as a Possible Site for Gene Therapy", Abstract, 16F *J. Cell. Biochem.* 48 (1992).
MacGregor et al., "Histochemical Staining of Clonal Mammalian Cell Lines Expressing *E. coli* β Galactosidase Indicates Heterogeneous Expression of the Bacterial Gene", 13 *Som. Cell Mol.* Genetics 253–265 (1987).
Price et al., "Lineage Analysis in the Vertebrate Nervous System by Retrovirus–Mediated Gene Transfer", 84 *Proc. Natl. Acad. Sci. USA* 156–169 (1987).
Gutierrez et al. 1992. The Lancet. 339:715–721.
Ledley, 1991. Human Gene Therapy 2:77–83.
Nabbl et al. 1989. Science 244:1342–1344.
Guyton (EDS), 1981 in "Textbook of Medical Physiology", W.B. Saunders Co., Philadelphia, pp. 819–822.
Wyngaarden et al., (EDS.) 1988. in "Cecil Textbook of Medicine", W.B. Saunders Co., Philadelphia, pp. 440–442.
The Merck Index, Ed. By Windholz et al. 1983 by Merck & Co., Inc. N.J., p. 13.

*Primary Examiner*—Brian R. Stanton
*Attorney, Agent, or Firm*—Fulbright & Jaworski LLP

[57] ABSTRACT

Method for in vivo introduction of a nucleic acid cassette into stem cells of intestinal epithelium. The nucleic acid cassette is introduced via vector solution. The vector solution can be delivered via the intestinal lumen in a variety of ways, including through an insertion device such as an endoscope, through catheters, through ligating and clamping the intestine after laparotomy or through slow release capsules. The vector solution once introduced into the intestinal epithelium is allowed to contact the stem cells for sufficient time for incorporation, usually between 1 and 48 hours. After sufficient incorporation, the insertion device and/or clamping and ligation procedure blockage are removed. Preferably, the procedure includes sufficient fluid to distend the intestine and provide additional access to the stem cells and the crypts. The procedure is useful in treating a variety of diseases including metabolic disorders, endocrine disorders, circulatory disorders, coagulation disorders, cancer, and gastrointestinal disease.

28 Claims, 2 Drawing Sheets

HISTOCHEMICAL ASSAY FOR β-gal
IN FROZEN SECTION FROM UPSTREAM
CONTROL SEGMENT.
MAGNIFICATION = 132X HISTOCHEMICAL ASSAY FOR β-gal
IN FROZEN SECTION FROM EXPERIMENTAL
SEGMENT OF THE SAME ANIMAL SHOWN IN FIG. 3.
MAGNIFICATION = 132X

GENE THERAPY USING THE INTESTINE

This application is a continuation of application Ser. No. 07/862,882, filed 04/03/92, now abandoned.

The invention described herein was developed in part with funds provided by the United States Public Health Service of the Department of Health and Human Services, Grant Number R-37 HD-14094. The Government has certain rights.

FIELD OF THE INVENTION

The present invention relates to the transduction of stem cells in the intestinal epithelium for the treatment of genetic disease. More particularly, it is related to in vivo targeting of RNA or DNA into the stem cells. It further relates to methods for the in vivo introduction of nucleic acids into stem cells for the treatment of genetic disease.

BACKGROUND OF THE INVENTION

The intestinal epithelium is a particularly attractive site for gene therapy because of its great mass of cells and its ease of access via the intestinal lumen. To understand these points we need to recall critical aspects of the morphology and kinetics of this epithelium. Its lumenal surface interfaces with the external milieu whereas its basolateral surface interfaces with the internal milieu. This means it is ideally located to receive nucleic acids applied externally (via the lumen) and to direct the protein or peptide products either: a) to the luminal surface (e.g., to correct a defect of digestion or absorption); b) to be secreted from the luminal surface (to act on the epithelium at more distal sites); c) to the interior of the epithelial cells (to act metabolically) or d) to the basolateral surface for secretion into the circulatory system (to act systemically).

The surface area of the intestinal epithelium is greatly increased by the presence of long, tongue-like structures known as villi. The epithelial villus cells are replaced continuously with cells emerging from the crypts (pit-like structures) that surround the base of the villi. Each villus is fed by ten or more crypts. Proliferation is confined to the lower two-thirds of the crypt and the progenitors of both crypt and villus cells are the stem cells located at the base of the crypt. Thus, with respect to gene therapy there are two general possibilities with this epithelium: a) permanent expression of the transferred gene as a result of transduction of the stem cells; or b) transient expression as a result of transduction or transfection of other crypt or villus cells. Whilst most applications favor permanent expression there are also some applications which arise from transient expression.

The final aspect of intestinal structure is its substantial length. This means there is a very large mass of tissue available for gene transfer. Moreover, the longitudinal character offers a high degree of precision with respect to the dosing of an introduced gene. The present invention provides a method for the in vivo targeting of the intestinal epithelium for the introduction of nucleic acids. Thus, it provides the first opportunity to modify the intestinal cells to treat human disease.

SUMMARY OF THE INVENTION

An object of the present invention is provision of a method for the in vivo introduction of a nucleic acid cassette into stem cells of intestinal epithelium via an insertion device.

An additional object to the present invention is an in vivo method for the introduction of a nucleic acid cassette via catheters.

A further object of the present invention is a method for in vivo introduction of a nucleic acid cassette into stem cells of intestinal epithelium via a clamp or a ligating procedure.

An additional object of the present invention is an in vivo method of introduction of a nucleic acid cassette into stem cells of intestinal epithelium using a DNA vector.

A further object of the invention is a method for in vivo introduction of a nucleic acid cassette into the stem cells using a viral vector.

An additional object of the present invention is a method of treating metabolic diseases by introducing a nucleic acid cassette into stem cells of intestinal epithelium.

A further object of the present invention is a method for treating endocrine disorders by introducing a nucleic acid cassette into stem cells of intestinal epithelium.

An additional object of the present invention is a method for treating deficiencies of circulatory proteins by introduction of a nucleic acid into the intestinal epithelium stem cells.

A further object of the present invention is the treatment of disaccharidase intolerance by the introduction of a nucleic acid cassette into the stem cells of the intestinal epithelium.

An additional object of the present invention is the treatment of colon cancer by the introduction of gene encoding a drug or antisense RNA into the stem cells of the intestinal epithelium.

An additional object of the present invention is as a vaccination method for viral or parasitic infections of the intestinal tract following transient transfection of an appropriate antigen.

Thus, in accomplishing the foregoing objects, there is provided in accordance with one aspect of the present invention, a method for in vivo introduction of a nucleic acid cassette into stem cells of the intestinal epithelium comprising the steps of introducing an insertion device into a segment of the intestine; introducing a vector solution via the insertion device, said vector solution containing the nucleic acid cassette; contacting the vector solution with the stem cells for sufficient time to incorporate the nucleic acid cassette into the stem cells; and removing the insertion device.

In an alternate embodiment of the present invention for the in vivo introduction of a nucleic acid cassette into stem cells of intestinal epithelium the insertion device contains a blocking means to isolate a segment and regulate the movement of fluid in the isolated segment.

In the preferred embodiment sufficient vector solution is introduced into the isolated segment to distend the intestine.

In alternate embodiments of the present invention the vector solution can be inserted by means of a catheter, or the clamping and ligating of the intestine and then the introduction of the vector solution.

The vector solution can be introduced either into the small intestine or the large intestine. In the case of circulatory protein introduction into the ileum is preferred.

An alternate embodiment of the present invention is the introduction of the nucleic acid by coating the vector in a slow-release capsule and introducing the capsule into the intestine.

The viral vectors and DNA vectors of the present invention are linked with appropriate elements such that the nucleic acid cassette will be expressed and a protein will be produced once the vector has been inserted into the stem cells of the intestinal epithelium. The present invention will be useful for the treatment of disaccharidase intolerance, pernicious anemia, ileitis or ileo-resection, hemophilia, circulatory protein defects, diabetes, endocrine disorders and metabolic diseases.

In a preferred embodiment of the present invention, the method of introducing a nucleic acid cassette into stem cells further comprises the step of adjusting the dose of the introduced nucleic acid cassette. The adjusting method comprises the steps of introducing the nucleic acid cassette into the stem cells of a segment of the intestine and testing for the degree of expression of the nucleic acid cassette from the stem cells. The introduction and testing steps are repeated until the desired level of expression is achieved. In one embodiment of the present invention, the segment is changed for each introduction step.

Other and further objects, features and advantages will be apparent from the following description of the presently preferred embodiments of the invention which are given for the purpose of disclosure when taken in conjunction with the accompanying drawings.

Figure 1A:
FIG. 1A is a schematic representation of a full but not distended intestine.

The drawings are not necessarily to scale and certain features of the invention may be exaggerated in scale and shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and spirit of the invention.

The nucleic acid cassette can be introduced into the stem cells of the intestinal epithelium by a variety of ways including transformation, transfection and transduction.

The terms "transformed" or "transformation" as used herein, refers to the process or mechanism of inducing transient or permanent changes in the characteristics (expressed phenotype) of a cell by the mechanism of gene transfer whereby DNA is introduced into a cell in a form or expresses a specific gene product or alters the expression of endogenous gene products.

The term "transfection" as used herein, refers to the process of introducing a DNA expression vector into a cell. Various methods of transfection are possible including microinjection, $CaPO_4$ precipitation, lipofection (liposome fusion), use of a gene gun.

The term "transduction" as used herein, refers to the process of introducing recombinant virus into a cell by infecting the cells with a virus particle. In the preferred embodiment of the present invention, transduction is used to introduce the nucleic acid cassette into the stem cells of intestinal epithelium.

The term "transient" is used, for example, in transient transduction relates to the introduction of genes into the stem cells of the intestinal epithelium to express specific proteins peptides, etc., where the introduced genes are not integrated into the whole cell genome and are accordingly eliminated from the cell over a period of time. Transient expression relates to the expression of gene products during the period of transient transfection. Transient expression could also be achieved by direct transfection of crypt or villus cells (i.e., other than stem cells).

The term "stable" is used, for example, in stable transduction refers to the stable introduction of genes into the chromosomes of the targeted cell where it integrates and becomes a permanent component of the genetic material in that cell. Gene expression after stable transduction can permanently alter the characteristics of the cell leading to stable transformation. An episomal transformation is a variant of stable transformation in which the introduced gene is not incorporated in the whole cell chromosome provided it is replicated as an extra chromosomal element. This can lead to apparently stable transformation of the characteristics of a cell.

The term "nucleic acid cassette" as used herein, refers to the genetic material of interest which can express a protein, polypeptide or RNA and which has been incorporated transiently, permanently or episomally into the stem cells of intestinal epithelium. The nucleic acid cassette is positionally and sequentially oriented in a recombinant retrovirus or a DNA vector with other necessary elements such that the nucleic acid in the cassette can be transcribed and, when necessary, translated into protein in the transformed stem cells of the intestinal epithelium.

The term "stem cell" as used herein, refers to those cells found in the crypts which are the progenitors of the epithelial cells found on the intestinal villi surface. "Crypts" as used herein refers to the crypts of Lieberkühn which are pit-like structures that surround the base of the villi in the intestine.

Genetic material which is incorporated into the stem cells according to the methods described herein can be any DNA or RNA. For example, nucleic acid can be: (1) not normally found in intestinal epithelial stem cells; (2) normally found in intestinal epithelial stem cells, but not expressed at physiological significant levels; (3) normally found in intestinal epithelial stem cells and normally expressed at physiological desired levels in the stem cells or their progeny; (4) any other DNA which can be modified for expression in intestinal epithelial stem cells; and (5) any combination of the above.

A variety of protein and polypeptides can be expressed by the nucleic acid cassette in the transformed intestinal epithelial stem cells, including proteins for treating metabolic disorders, and endocrine disorders. Examples of proteins are phenylalanine hydroxylase, insulin, anti-diuretic hormone and growth hormone. Disorders include phenylketonuria, diabetes, organic acidurias, tyrosinemia, urea cycle disorders, familial hypercholesteremia. Genes for any of the proteins or peptides which can correct the defects in these disorders can be introduced into stem cells such that the protein or peptide products are expressed by the intestinal epithelium. Coagulation factors such as antihemophilic factor (factor 8), Christmas factor (factor 9) and factor 7 can likewise be produced in the intestinal epithelium. Proteins which can be used to treat deficiency of a circulatory protein can also be expressed in the intestinal epithelium. These can be, for example, albumin for the treatment of an albuminemia, alpha-1-antitrypsin, hormone binding protein. Additionally, the intestinal symptoms of cystic fibrosis can be treated by inserting the gene for the normal cystic fibrosis transmembrane conductance regulator into the stem cells of intestinal epithelium. Abetalipoproteinemia can be treated by the insertion of the apolipoprotein B. Disaccharidase intolerance can be treated by the insertion of sucrase-isomaltose, lactase-phlorizin hydrolase and maltase-glucoamylase. The insertion of the intrinsic factor for the absorption of vitamin $B_{12}$ or the receptor for the intrinsic factor/cobalamin complex for absorption of vitamin $B_{12}$, as well as the transporter for bile acids can be inserted into the intestinal epithelium. Further, any drug which can be encoded by nucleic acid can be inserted into the stem cell of the intestinal epithelium to be secreted in localized, high concentrations for the treatment of cancer. In this respect, one skilled in the art will readily recognize that antisense RNA can be encoded into the stem cells after production of antisense it can incorporate into the cancerous cells for the treatment of cancer.

The term "DNA vector" as used herein, refers to a DNA vector which includes the following elements linked sequentially at appropriate distances to allow for the functional gene expression of the nucleic acid cassette. The DNA vector will have a promoter, a 5' mRNA leader sequence, an initiation site, the nucleic acid cassette, wherein the cassette has a restriction site, a 3' untranslated region and a polyadenylation signal. One skilled in the art will readily recognize that these elements must be in specific orders and specific distances in order to obtain expression. The order and sequences is partly dependent upon what gene is to be expressed as well as the specific elements used.

In the present invention, an alternate embodiment for the introduction of the nucleic acid cassette into the stem cells is the use of a virus vector. The virus can be selected from a wide variety of groups, including gastrointestinal viruses such as parvovirus, rotavirus and Norwalk virus and any other viruses which cause gastrointestinal disease. In addition, the virus can be also selected from groups consisting of the adenovirus and adeno-associated viruses. In the preferred embodiment, retrovirus is used. When a retrovirus is used, it can be selected from any of the groups of amphotropic, xentropic, ecotropic, polytropic, gibbon ape, and any recombinant or designed retrovirus. As an example, when a retroviral vector is used, the vector consists of RNA comprised of the following elements linked sequentially at appropriate distances for allowing functional gene expression. Generally, the gene of interest, nucleic acid cassette in the present invention, is cloned downstream of a retroviral LTR in a vector lacking key retroviral genes, the product which are supplied in trans by a defective helper virus. On entry into the host cell, the retroviral vector is reversed transcribed and can integrate into the host genome. One skilled in the art will readily recognize that substituting the other viruses appropriate promoters and enhancers must be inserted into the structure in order to express the nucleic acid cassette.

In the present invention, in both the viral vector and the DNA vector, the nucleic acid cassette is activated with a promoter. The promoter used is any of a wide variety of promoters known in the art. Examples of these promoters which are used in the present invention include the LTR promoter, cytomegalovirus promoter, malate dehydrogenase promoter, dihydrofolate reductase promoter, and the adenosine deaminase promoter. In enhanced and preferred embodiments of the present invention, intestinal specific promoters such as the intestinal fatty acid binding protein promoter, the disaccharidase promoters, cystine-rich intestinal protein promoter and apolipoprotein promoter are used. Examples of the disaccharidase promoter include the sucrase-isomaltase, the maltase-glucoamylase promoter and the lactase-phlorizin hydrolase promoter. The apolipoprotein promoter can be selected from the group consisting of apolipoprotein-B promoter, apolipoprotein-A-I promoter, apolipoprotein-A-II promoter and apolipoprotein-A-IV promoter.

One skilled in the art will recognize that the selection of the promoter will depend on the vector, the cell type and the nucleic acid cassette. One skilled in the art will also recognize that in the selection of the promoter, the parameters can include: achieving sufficiently high levels of gene expression to achieve a physiological effect; maintaining a critical steady state of gene expression; achieving temporal regulation of gene expression; achieving tissue specific expression; achieving pharmacological, endocrine, parocrine or autocrine regulation of gene expression; and preventing inappropriate or undesirable levels of expression. Any set of selection requirements will depend on the conditions, but can be readily determined once specific requirements are determined. Those promoters which are naturally active in the intestinal epithelium itself are the preferred promoters.

In order to enhance the uptake of the nucleic acid cassette into the stem cells of the intestinal epithelium and to facilitate the incorporation of the nucleic acid cassette, it has been found that the addition of a "proliferation enhancing factor" with the virus or DNA vector is helpful.

As used herein the "proliferation enhancing factor" refers to those factors which: (1) enhance or facilitate proliferation of the stem cells, and/or (2) enhance the uptake and incorporation of the viral or DNA vector into the stem cells. The proliferation enhancing factors which are preferred in the present invention include epidermal growth factor, angiogenesis factor, insulin-like growth factor-1, insulin-like growth factor-2, transforming growth factor-α, and gastrin. In addition, the proliferation enhancing factor can include a drug. The drugs which are recommended consist of methotrexate, fluorouracil, floxuridine, and arabinoside-C. By enhancing the proliferation, you increase the ability of the nucleic acid cassette to be incorporated into the stem cells. Some of the enhancing factors work by stimulating the growth of the intestinal epithelium. Other factors work by destruction of the intestinal epithelium which results in a compensatory increase in proliferation of the stem cell compartment. For example, the later case is seen with the use of drugs. One skilled in the art will readily recognize that there are other proliferation enhancing factors which can be used and which will be useful in this invention.

As used herein, the term "vector solution" refers to the solution containing the viral or DNA vectors. Such solution can be any of the common solutions used for introducing vectors into cells. For example, the present invention for the introduction into the intestine the solution is preferably composed of the following: Dulbecco's modified Eagle's medium (DMEM) containing 8 $\mu$g/ml of the detergent polybrene.

Other agents such as mucolytic agents can be useful in improving the accessibility of the vector to the intestinal stem cells. Examples of mucolytic agents include N-acetylcysteine, dithiothreitol, pepsin and pilocarpine.

One embodiment of the present invention includes a method for in vivo introduction of a nucleic acid cassette into stem cells of intestinal epithelium comprising the steps of: introducing an insertion device into a segment of the intestine; introducing a vector solution via the insertion device, said vector solution containing the nucleic acid cassette; contacting the vector solution with the stem cells for sufficient time to incorporate the nucleic acid cassette into the stem cells; and removing the insertion device.

Alternate embodiments for the in vivo introduction of the nucleic acid cassette into the stem cells of the intestinal epithelium have comprised the steps of introducing the insertion device into a segment of the intestine wherein the insertion device has a blocking means; expanding the blocking means to isolate a segment and to regulate the movement of fluid in the isolated segment; introducing via the insertion device sufficient vector solution into the isolated segment to distend the intestine, said vector solution containing the nucleic acid cassette; contacting the vector solution with the stem cells in the isolated segment for sufficient time to incorporate the nucleic acid cassette into the stem cells; and removing the insertion device and blocking means.

Alternate embodiments for the present invention for inducing nucleic acid into the stem cells intestinal epithelium comprise the steps of introducing exterior catheters into the intestine, infusion of vector solution containing the nucleic acid cassette through the intestine via the catheters for sufficient time for the nucleic acid cassette to incorporate into the stem cells and removing the catheters.

One skilled in the art will readily recognize that sufficient time means that the time for contact between the vector solution and the stem cells must be sufficient for the nucleic acid cassette to be taken up by the stem cells for incorporation. One skilled in the art will readily recognize that the longer the vector solution is there the greater the chances are of increasing the amount of incorporation. In the present invention times between 1 and 48 hours can be used.

In all the embodiments of introducing the nucleic acid cassette into the intestine, the vector solution can be introduced into the small intestine or into the large intestine. When introduced into the small intestine, it may be advantageous to introduce it into the ileum, especially for circulating proteins. For treating ileitis or ileal resection it can be advantageous to introduce the vector solution into the jejunum of the large intestine.

Another embodiment of the present invention for the in vivo introduction of nucleic acid cassette into a stem cell of the intestinal epithelium comprises the steps of ligating or clamping a section of the intestine such that it forms a closed cavity; injecting into the closed cavity sufficient vector solution to distend the intestine, wherein the vector solution contains a nucleic acid cassette; removing the ligation or clamp after about 4 hours. Again, sections of the small or large intestine can be ligated or clamped.

In the preferred embodiment the vector solution is introduced into the intestine is in sufficient quantity to cause distention of the intestine. Distention of the intestine opens the crypts providing access to the stem cells.

Another alternate embodiment for the in vivo introduction of nucleic acid cassette into stem cells of the intestine comprises the step of introducing a slow release encoded capsule into the intestine wherein the capsule contains a vector having nucleic acid cassette. As the slow release encoded capsule deteriorates, the vector solution is released into the intestinal cavity and allowed time to contact with the stem cells for the introduction of the cassette into the stem cells.

The insertion device used in the present invention can be any of the commonly available devices. In the preferred embodiment the insertion device is an endoscope. In the preferred embodiment the endoscope has blocking means and the blocking means are balloons positioned along the endoscope at a distance from each other so that when inflated they isolate a segment of the intestine. While using a blocking means they are able to regulate the introduction of fluid and the movement of fluid in and out of the isolated segment.

In some embodiments of the present invention the nucleic acid cassette is introduced into a plurality of segments. In this procedure the method comprises the steps of blocking each separate segment with the blocking means introducing into each blocked section a vector solution containing a nucleic acid cassette.

In the most preferred embodiment of the present invention for the in vivo method of introducing a nucleic acid cassette into stem cells of the intestinal epithelium the further step of adjusting the dose of the nucleic acid cassette which is introduced into the stem cells is added. In the step of adjusting the dose, the nucleic acid cassette is introduced into the segment of the intestine; testing of the degree of expression in the nucleic acid cassette into the stem cells is then performed. Then, depending on the results of the test, the introducing step is repeated. The introducing and testing steps are repeated until the desired level of expression is achieved. Examples of methods for testing for the expression include the following: if the nucleic acid cassette encoded: a) insulin, blood glucose would be measured; b) ornithine transcarbamylase (a urea cycle enzyme), blood ammonia would be measured; c) $\alpha$-1-antitrypsin, circulating $\alpha$-1-antitrypsin would be measured; d) disaccharidase, ability to digest that disaccharide would be measured.

The introducing step of the adjusting of the dose step can be done in a variety of ways. In one method the same segment is reiteratively contacted with the vector solution. In an alternate embodiment different sections of the intestine are sealed for the introduction step. One skilled in the art will readily recognize that any combination of successive introduction in the same segment or introduction into different segments can be performed.

Another embodiment of the present invention is a method of transiently introducing a cassette into the stem cells or their progeny. This method is useful in vaccination against intestinal infection from virus, bacteria or parasites. In this procedure the nucleic acid cassette encodes a sequence for a protein or polypeptide from a virus, bacteria or parasite. The protein is expressed in the cell and secreted into the intestinal lumen where it stimulates production of secretory immunoglobulins.

The following examples are offered by way of illustration and are not intended to limit the invention in any manner:

EXAMPLE 1

Introduction of DNA into Intestinal Stem Cells with the Retrovirus

A rat is subjected to laparotomy and a section of the small intestine is emptied of contents by gentle compression and then ligated with coarse tread. The vector solution is introduced into the ligated segment. In order to identify the ligated segment at the time of sacrifice, "landmarks" are put just outside the ligatures by using single sutures of 5.0 silk in the intestinal wall. The incision is closed and the animal is allowed to regain consciousness. To avoid prolonged anesthesia, which might have a suppressive effect on intestinal function, the inhalation anesthetic isofluorane is used.

The anesthetic allows extremely rapid induction of, and recovery from, anesthesia. Typically, the rats are walking around in about 2 to 3 minutes after being returned to their cages. The anesthetic is also very safe.

After the initial surgery, the animals are allowed to drink but not eat. Four hours later, again using isofluorane anesthesia, the incision is re-opened and the ligatures are removed. This brief period of ligation generally causes neither acute nor chronic damage to the small intestine.

The choice of a four-hour ligation period is based on several considerations. First, this is short enough to preclude any discomfort due to accumulation of chyme proximal to the first ligature. Also, it is short enough to insure that high numbers of live retrovirus are available for infection throughout the duration of ligation. The half-life of retrovirus at 37° C. has been established to be approximately six hours. Finally, within a four-hour period, a sufficient amount of viral infection occurs. It is known that synthesis of a viral DNA is facilitated by cell division and integration into the host DNA occurs only during the S phase of the cell cycle. It is assumed that only cells which initiate DNA synthesis during the four-hour infection period are successfully transduced. Since the cell cycle of intestinal stem cells has been estimated to be 24 hours, approximately ⅙ of the stem cells capable of retroviral transduction with this protocol. With 16 stem cells per crypt, this means an average of two to three stem cells per crypt are transduced.

EXAMPLE 2

Accessibility of Intestinal Crypts

Figure 1B:
FIG. 1B is a schematic representation of a considerably distended intestine.

Regular histological sections show the intestine in a non-distended state and give the impression that the crypts are deeply buried and quite inaccessible. When the intestine is distended, however, there are significant changes of architecture such that the crypts appear to be much more accessible. To demonstrate this phenomenon, solution was added to ligated segments (see Example 1) such that the segments were either full but not distended, or considerably distended. The results are schematically shown in FIG. 1A, no distention and FIG. 1B, distended intestine. In these positions, the intestinal sections were frozen and subject to cryostatic sectioning. The degree of distension caused no damage to the intestine when assessed immediately following ligation or several days later. In similar studies, where vital stain methylene blue was added to the culture medium, staining of the crypt cells was greatly enhanced when the segment was distended.

EXAMPLE 3

Effect of Intestinal Sections on Viability of Retroviruses

To measure the viability of retroviruses, culture medium was placed in the ligated segment for a four-hour period and then removed. The intestinal effluent was then incubated for four hours in vitro at 37° C. with retrovirus of known titer. This procedure simulates the in vivo exposure of the virus to any deleterious substances, such as proteases in intestinal secretions. After the incubation, the retroviral titer was determined on NIH3T3 cells in the standard manner. This was found to be 44% of that of control retrovirus which was incubated 4 hours with culture medium instead of intestinal effluent. Thus, a little over half of the retroviral particles appeared to be inactivated during a four-hour exposure to intestinal secretions. This does not represent a serious loss, especially in view of the evidence that binding of ecotropic retroviruses to the cell surface receptor is relatively fast (1.5–2 hours) and internalization is even faster (10 minutes).

EXAMPLE 4

Gene Transfer into Intestinal Epithelial Cells

For this study, a retrovirus with a reporter gene was prepared. The reporter gene can be detected histochemically, thus, allowing identification of cells within the intestinal mucosa which express the transferred gene. The study used a very sensitive and commonly used reporter for histochemical analysis, the bacterial β-galactosidase (β-gal). The specific vector used was Zen$^+$β-gal in which the β-gal gene is under the control of the viral long-term repeat (LTR) and the viral enhancer is intact. Zen$^+$β-gal is a recombinant derivative of Moloney murine leukemia virus. It was propagated in the ecotropic packaging cell line GP+E86 and routinely yielded titers in the order of 2–3×10$^5$ per ml. when assayed on NIH3T3 cells. The viral construct lacks the gag, pol, and env regions and therefore is replication incompetent. The packaging cell line was routinely checked and found to be devoid of helper virus.

To test for feasibility of retroviral transduction, IEC-6 cells (an intestinal crypt cell line) were exposed to the vector solution with Zen$^+$β-gal under standard conditions normally used for titering. Successful transduction was achieved and titers were approximately 20% of those seen in NIH3T3 cells, the regular titering cell line which was run in parallel. This demonstrates that the rat intestinal crypt cells are capable of transduction in vitro.

EXAMPLE 5

Transduction of Adult Small Intestine with Zen$^+$ β-Gal

Although ligated segments can be placed anywhere along the length of the small intestine, these experiments have focused on the ileum. With an incision in the appropriate place, the ileocecal junction immediately presents itself, making it easy to adopt a standard positioning of 5 cm proximal to that junction for placement of ligated segment. The ileum offered the advantage for this study that brush border lactase activity is low in this region of the adult intestine, thus minimizing problems of detection of the bacterial β-gal. Sufficient vector solution was introduced into the ligated segments to cause distension (see Example 1). Ligatures were removed four hours later and the animals were sacrificed six days after surgery.

At the time of sacrifice, the ligated segment as well as the control segment taken 10 cm proximally were frozen for cryostat sectioning. Sections (4$\mu$) were made transverse to the longitudinal axis of the small intestine. β-gal was detected histochemically using the chromogen X-GAL as a substrate under standard conditions. (MacGregor, GR et al. *Som. Cell Mol. Genetics* 13:253–265 (1987). As a positive control, a section of transgenic mouse liver expressing β-gal was run with each set of intestinal sections. The slides were blinded and scored by three independent observers for the number of positive epithelial cells per intestinal cross-section. A cell scored positive only if it displayed the blue reactive product throughout the cytoplasm. This eliminates contributions from endogenous lactase, which is confined to the brush border of villus epithelial cells. Scores from the three observers were averaged and given a single value for each tissue section. Means and standard errors were calculated from the number of individual animals used.

Figure 2:
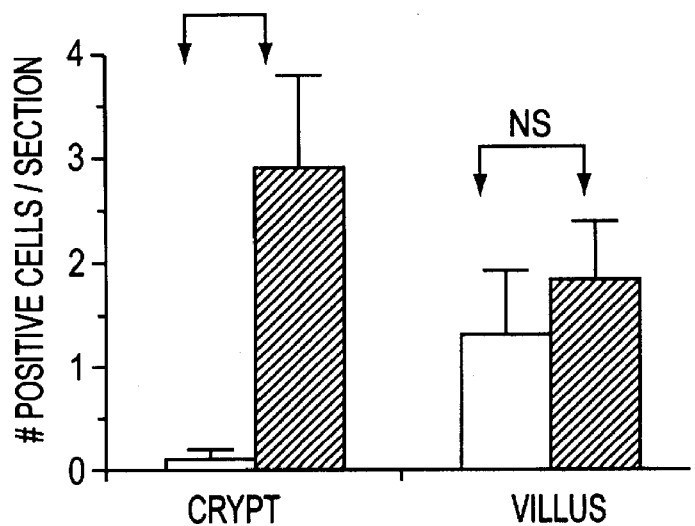
FIG. 2 is a histogram of β-gal activity.

The results of the scoring are shown in FIG. 2. It can be seen that a highly significant number of positive cells were found in the crypt epithelium of experimental sections. As was seen in FIG. 2, the background in the villus is higher than in the crypts. While this limits the sensitivity of the β-gal reporter in the villus region, it is not a serious limitation. Because the reporter is expressed in all the progeny of each transduced stem cell, there will be a 16-fold amplification as a result of the four cell divisions that occur in the proliferation zone.

While the average number of positive cells per section may appear low in FIG. 2, it actually represents a relatively high efficiency of transduction, because the estimated number of retrovirus particles per section is approximately 20. This is calculated as follows: viral titer=$1.5 \times 10^5$/ml; volume introduced=1.0 ml/3 cm segment; therefore, number of virus particles available=$1.5 \times 10^5$/3 cm=$0.5 \times 10^5$/cm=$5/\mu$. Thus, the number available to a $4\mu$ section=20. Therefore, the average of three transductions per section in FIG. 2 represents an efficiency of 15%. This in vivo transduction efficiency of 15% is almost as high as the 20% seen in the in vitro studies using IEC-6 cells (see Example 4). In the in vivo experiments, the number of virus particles was limiting, and thus, to achieve higher "hit" rates in the intestine it is necessary to use concentrated retroviral solutions.

Figure 3:
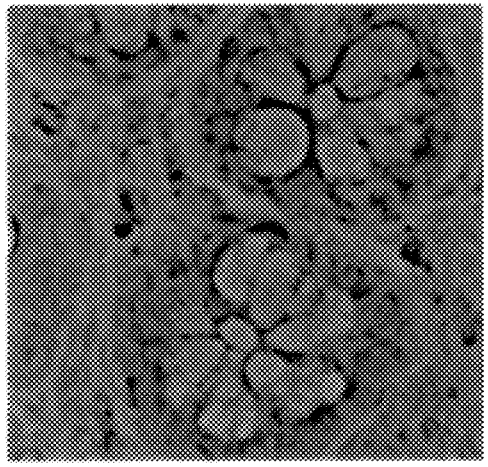
FIG. 3 shows the results of histochemical assay of β-gal in controls.
Figure 4:
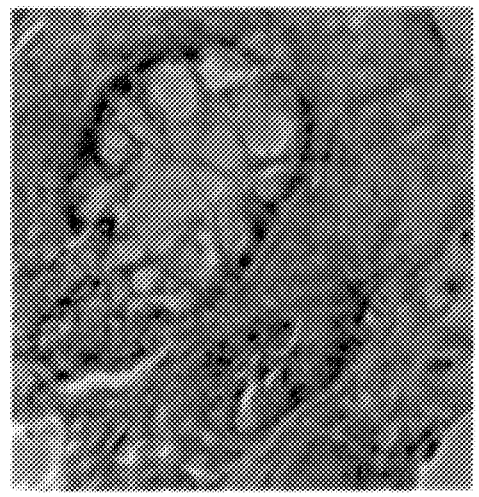
FIG. 4 shows the results of histochemical assay of β-gal in animals after transduction.

Histological sections from control and experimental tissues of one of the animals represented in FIG. 2 are shown in FIG. 3 (control) and FIG. 4 (experimental). Although sectioning was performed transverse to the long axis of the intestine, the tendency of the outer edges of the segment to curl back onto themselves, due to contraction of the longitudinal muscle layer, indicates that crypts and villi were seen transversely rather than longitudinally. The control section, FIG. 3, shows crypts in complete cross-section, whereas the experimental section, FIG. 4 is somewhat at an angle. Note the control picture shows no blue reaction product, whereas the experimental section, that is the ligated section which was subject to retroviral infection, has several cells with distinct positive reaction in the cytoplasm. Because of the angle, the experimental section shows positive cells at three different levels of the crypts. The uppermost crypt is sectioned somewhere near the middle; the second crypt is sectioned close to the base; and the lower crypt is sectioned right at the base. Presence of positive cells in all three locations indicates that transduction occurs in the stem cells. Sham operated animals, that is, animals in which the ligated section receive culture medium without retrovirus also showed no blue epithelial cells.

EXAMPLE 6

Alternative Reporter Gene

As an alternative to the β-gal reporter gene, an additional reporter which does not show up endogenous activity in the intestine was developed. The bacterial enzyme chloramphenicol acetyl transferase (CAT) was used. Even though CAT does not show endogenous activity in the intestine, it can be detected in the tissue extracts with high sensitivity by quite simple procedures. Further, it also can be detected immunohistochemically and thus, in any situation where particularly high CAT activity was detected biochemically, the specific cells expressing CAT can be verified immunohistochemically. A further advantage of CAT over β-gal is that CAT immunohistochemistry can be performed on paraffin sections, which give much better morphology than the cryostat sections used for β-gal.

Figure 5:
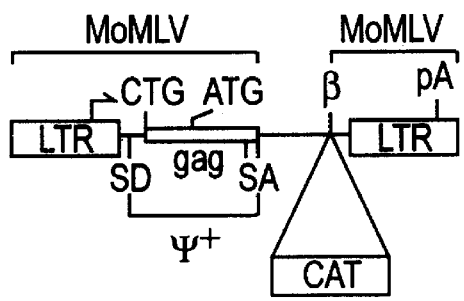
FIG. 5 is a schematic of the CAT plasmid.

The CAT plasmid shown in FIG. 5 was constructed. It is a simple derivative of Moloney murine leukemia virus (MoMLV) in which transcription of the CAT insertion is driven by the viral LTR. The plasmid efficiently expresses CAT activity following electroporation into NIH3T3 cells and is ready to be transfected into the ecotropic retroviral package and cell line.

A second plasmid bearing the neomycin-resistant gene (neo) is co-transfected in order to allow selection of transformants. After viral producing cells are obtained, the resulting replication-defective CAT retrovirus is assessed for titer and stability in NIH3T3 cells. The CAT retrovirus is used in place of the β-gal retrovirus.

EXAMPLE 7

Optimization of the Process for Gene Transfer into Intestinal Epithelium

In order to optimize the use of retrovirus vectors, the individual steps that are involved in transduction via these vectors need to be considered. The steps comprise (1) binding to membrane receptors; (2) internalization of the receptor-bound virus; (3) synthesis of viral DNA via a reverse transcriptase; (4) integration of the proviral DNA into the host chromosome; and (5) expression of the integrated DNA. Although all of these parameters can be adjusted, steps (1), (4) and (5) are studied because they are the most amenable to enhancement. The gene transfer experiments are directed towards the receptor in the crypt stem cells. Thus, it is important that there be a method to detect the RNA in a particular subset of cells. An example of the detection method is in situ hybridization. Frozen sections are prepared from the duodenum, jejunum and ileum of rats aged 7, 14, 21, 28 and 42 days. They are hybridized with the $^{35}$S antisense riboprobe prepared from the plasmid pJET. This plasma contains the cDNA for the murine ecotropic retroviral receptor. Controls for non-specific binding include serial sections hybridized with sense riboprobes prepared from the same plasmid. Prior to use for in situ hybridization, the antisense riboprobe is used in Northern blots to check that the appropriate sized transcripts, 9.0 and 7.5 kb, are detected.

A number of factors can limit the interaction of the retroviral and the viral receptors on the crypt stem cells. The two most common are the concentration of the retrovirus and trapping by mucous. These can be addressed by using concentrated viruses and a mucolytic agent, respectively. In the previous examples, supernatants from viral-producing cells were used directly. The supernatants had titers in the order of $10^5$/ml. Calculations indicated that the number of retrovirus particles is probably the limiting factor. Moreover, when it is considered that some proportion of retroviruses might effectively be lost through non-specific binding to the mucous layer, it becomes clear that the effective viral concentration in the vicinity of the intestinal stem cells is extremely low. Thus, by concentrating the retrovirus, the amount of transduction can be increased. Also by the addition of a mucolytic agent, the amount of transduction can be increased.

The retrovirus is concentrated by centrifuging supernatants from viral producing cells of 14,000 g. overnight as described in Price, et al., Proc. Nat'l. Acad. Sci. USA 84: 156–169 (1987). If the viral pellet is made up in 1/100 of the original volume, titers can be increased 50-fold. No more than half the retroviruses are inactivated during centrifugation. Concentrated viral stocks are introduced into ligated intestinal segments in the standard manner. Activity of the reporter gene per mg intestinal protein allows assessment of the effective viral concentration. Controls in the experiments are animals receiving a portion of the same viral stock prior to concentration.

To control for trapping by mucous, mucolytic agent, N-acetylcysteine (NAC) is used. This substance is well known for its ability to reduce the viscosity of mucous via reduction of the disulfide bonds. Furthermore, it can be used in vivo, and indeed, is used clinically for certain conditions of the gastrointestinal tract. When administered enterally at a concentration of 5 mM, in addition to its acute effect on mucous viscosity, it appears to have a chronic effect wherein mucous production is reduced. Affected tissue is harvested 1 to 6 days later to quantitate the immediate and prolonged expression of the reporter gene. Concentrations of 5 mM NAC have no adverse effects on viability of the retrovirus.

For the optimization of integration of the transferred genetic material specific agents which stimulate intestinal proliferation are examined. These include pharmacologic agents such as anti-cancer drugs and physiological agents such as hormones and growth factors. The pharmacologic agents stimulate proliferation of a much greater rate than physiological agents. Thus, the primary enhancement or stimulation of epithelial proliferation involves using anti-cancer drug methotrexate, fluorouracil, floxuridine and arabinoside-C. Following a single injection of arabinoside-C (400 mg./kg., ip), the intestinal crypts display a biphasic response. Initially, there is elimination of cells that are actively dividing; subsequently, there is a regeneration phase during which mitotic activity is substantially elevated over control levels. A peak of DNA synthesis is observed 14 hours after ingestion. This suggests partial synchrony of the cycling in the surviving cells. The distribution of the regenerative response along the crypt column suggests that the entire proliferative compartment behaves as stem cells under these conditions. These features of arabinoside-C action make it particularly attractive for pretreatment of the intestine to facilitate transduction of intestinal stem cells.

EXAMPLE 8

Alternative Method

In previous examples, a four-hour infection protocol was used. In order to increase the duration of the contact time between the vector solution containing the retrovirus and the intestinal epithelium, the simplest approach would be to use a longer time period. However, there are two problems with this approach. The ligation may cause discomfort in the animals due to the accumulation of chyme above the first ligature. Also, since the half-life of the retrovirus at 37° C. is approximately six hours, simply lengthening the ligation period would be associated with diminishing returns due to falling virus titers. To alleviate both these problems, a surgical preparation in which a bypassed intestinal segment is cannulated at both ends was prepared. This procedure allows replacement of fresh retrovirus every four hours for periods up to 24 hours. Using this procedure, the tissue is still healthy four days after surgery. Further, the fact that the remaining intestine is re-anastomosed indicates that the animal can be allowed to fully recover from the surgery before infection of the bypassed segment is initiated. Thus, the introduction of the retrovirus can be accomplished in a conscious animal with minimal disturbance.

EXAMPLE 9

The Endoscope Method

The patient is appropriately pre-treated to empty the bowel region of the intestine in which transduction or gene therapy is to occur. The patient is then sedated. Either an upper or a lower endoscopy is used to place a tube with a port in the chosen region of the intestine. The upper route is used for the small intestine and the lower route for the large intestine. On the tube there is also a lower and upper balloon, which are inflated after the endoscope is in place. The vector solution is then added via the tube in a volume calculated to distend the blocked intestinal segment. After sufficient time has elapsed, the balloons are deflated and the tube is removed.

EXAMPLE 10

The Catheter Method

In this procedure, the patient is appropriately pre-treated to empty the bowel region of the intestine. The patient is then anesthetized. Inflow and outflow catheters are placed in a chosen region via laparotomy. The incision is closed and the catheters are exteriorized. The vector solution is infused for an appropriate period of time. The flow is regulated so that there is distension of the intestine during the infusion. The patient remains NPO during the fusion. The catheters are removed.

Alternatively, a dual-bore nasogastric tube with two balloons and two ports is introduced and allowed to pass to the region of interest. The balloons are then inflated. The vector solution is perfused in through the outer bore and the top port, and returned through the inner bore of the lower port. After an appropriate period of time, the perfusion is stopped, the balloons deflated and the tube removed. Again, the flow rate is adjusted so that there is distension of the intestine.

EXAMPLE 11

Ligation Method

The patient is appropriately pre-treated to empty the bowel region of the intestine. The patient is sedated and anesthetized. A laparotomy is performed in the chosen region of the intestine as identified. Broad, non-damaging ligatures or clamps are placed at proximal and distal ends of the chosen intestinal segment. The vector solution is injected in an amount to cause moderate distention. After four to six hours, the ligatures or clamps are removed and the patient is allowed to recover from the surgery.

EXAMPLE 12

Treatment of a Child with Phenylketonuria

The phenylalanine hydroxylase nucleic acid sequence is introduced via a vector solution into a given segment of the intestine using any one of the methods described herein. The patient is subsequently monitored to determine the effectiveness of the initial procedure by following the extent to which serum levels of phenylalanine fall toward the normal range. If serum levels do not fall within a normal range, the percentage of decrease is determined. Then the introduction procedure is repeated, either on the same segment of the intestine or for, more efficiency, another segment of the intestine is used. The length of the second segment to be used and the concentration of vector in the vector solution is determined by the amount of reduction still needed. Again, any one of the above procedures can be used for introducing the second dose of the vector solution. The patient is then monitored and the decrease toward normal determined. If further decrease is needed fine tuning can be achieved by a additional introduction. Each time the reintroduction is carefully recalibrated so that the amount of reduction can be carefully controlled.

Similar procedures can be used for correcting any of the urea cycle defects. In this case, success is monitored by measuring the reduction of blood ammonia. When correcting for a growth hormone deficiency, the extent to which serum levels approach the normal range can be monitored. It is important to remember that the longitudinal aspects of the intestine makes it much easier to calculate the appropriate follow-up dose once the initial gene transfer has been performed. Furthermore, the intestine offers an important margin of safety in case the calculations go wrong in the final gene transfer. If too many nucleic acid cassettes are introduced, and thus, there is an overdose situation, a portion of the treated intestine can be surgically removed. Intestine resections of this type are relatively routine and are certainly much more straightforward than resections in most other organs.

In the case of phenylketonuria, if the first dose resulted in a 25% reduction in serum phenylalanine levels, the second dose would be double the first and thus provide a further reduction in circulating phenylalanine, yielding a total of 75% reduction. The third calculation is carefully made on the size of the intestine so that a 100% reduction results.

All patents and publications mentioned in this specification are indicative of the levels of those skilled in the art to which the invention pertains. All patents and publications are incorporated herein by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. Transformed stem cells, viral vectors, DNA vectors, along with the methods, procedures, treatments, molecules and specific compounds described herein are presently representative of preferred embodiments, are exemplary and are not intended as limitations on the scope of the invention. Changes therein and other uses will occur to those skilled in the art which are encompassed within the spirit of the invention as defined by the scope of the claims.

What we claim is:

1. A method for in vivo introduction of nucleic acid cassette into intestinal epithelial progenitor cells or their progeny, comprising the steps of:
   introducing an insertion device into a segment of the intestine;
   introducing a vector solution via the insertion device, said vector solution containing the nucleic acid cassette;
   contacting said cells or their progeny with the vector solution for sufficient time to incorporate the nucleic acid cassette into said cells or their progeny; and
   removing the insertion device.

2. A method for in vivo introduction of a nucleic acid cassette into intestinal epithelial progenitor cells or their progeny, comprising the steps of:
   introducing an insertion device into a segment of the intestine, said insertion device having an expandable blocking means;
   expanding the blocking means to isolate a segment of the intestine and to passively regulate the movement of fluid in the isolated segment of the intestine;
   introducing via the insertion device sufficient vector solution into the isolated segment to distend the intestine, said vector solution containing the nucleic acid cassette;
   contacting said cells or their progeny with the vector solution in the isolated segment for sufficient time to incorporate the nucleic acid cassette into said cells or their progeny; and
   removing the insertion device and blocking means.

3. A method for in vivo introduction of a nucleic acid cassette into intestinal epithelial progenitor cells or their progeny, comprising the steps of:
   introducing exterior catheters into the intestine;
   infusing a vector solution containing the nucleic acid cassette through the intestine via the catheters;
   contacting said cells or their progeny with the vector solution for a sufficient time for the nucleic acid cassette to incorporate into said cells or their progeny; and
   removing the catheters.

4. The method according to claim 1, 2 or 3, wherein the sufficient time is about 1 to 48 hrs.

5. The method according to claim 1, 2 or 3, wherein the vector solution is introduced into the small intestine.

6. The method according to claim 1, 2 or 3, wherein the vector solution is introduced into the large intestine.

7. The method according to claim 1, 2 or 3, wherein the vector solution comprises a DNA vector, said DNA vector including the following elements linked sequentially at appropriate distances for allowing functional expression of the nucleic acid cassette: a promoter; a 5' mRNA leader sequence; nucleic acid cassette, wherein said cassette has a restriction site and encodes a nucleic acid sequence to be expressed; a three prime untranslated region; and a polyadenylation signal.

8. The method of claim 7, wherein the promoter is selected from the group consisting of a viral LTR promoter, cytomegalovirus promoter, malate dehydrogenase promoter, dihydrofolate reductase promoter, and adenosine deaminase promoter.

9. The method of claim 7, wherein the nucleic acid cassette includes an intestinal specific promoter.

10. The method of claim 9, wherein the promoter is selected from the group consisting of intestinal fatty acid binding protein promoter, disaccharidase promoter, cystine rich intestinal protein promoter and apolipoprotein promoter.

11. The method of claim 10, wherein the disaccharidase promoter is selected from the group consisting of sucrase-isomaltase promoter, maltase-glucoamylase promoter and lactase-phlorizin hydrolase promoter.

12. The method of claim 10, wherein the apolipoprotein promoter is selected from the group consisting of apolipoprotein-B promoter, apolipoprotein A-I promoter, apolipoprotein A-II promoter and apolipoprotein A-IV promoter.

13. The method according to claim 1, 2, or 3, wherein the vector is a virus.

14. The method according to claims 1, 2, or 3, wherein the vector is a retrovirus.

15. The method of claim 14, wherein the retrovirus is selected from the group consisting of amphotropic, xenotropic, ecotropic, polytropic, and gibbon ape.

16. The method according to claim 1, 2, or 3, wherein the nucleic acid cassette is transduced into a retrovirus producing cell line and said retrovirus producing cell line is introduced into the intestine.

17. The method according to claim 1, 2, or 3, wherein the nucleic acid cassette is an adenovirus or adeno-associated virus.

18. The method according to claim 1 or 3, wherein the amount of vector solution introduced is of sufficient quantity to cause distention of the intestinal wall.

19. The method of claim 1, wherein the insertion device includes a blocking means to isolate a segment of the intestine; and includes the further step of expanding the blocking means to block the movement of fluid into and out of an isolated segment of the intestine.

20. The method according to claim 2 or 19, wherein the insertion device is an endoscope and the blocking means are balloons positioned along the endoscope.

21. The method according to claim 1, 2, or 3, comprising the further step of adjusting a dose of the introduced nucleic acid cassette by adding additional vector solution into a single isolated segment of intestine.

22. The method of claim 21, wherein the adjusting step comprises:

introducing the nucleic acid cassette into a segment of the intestine;

testing for the expression the nucleic acid cassette in the intestinal epithelial progenitor cells or their progeny; and repeating the introducing and testing steps until a desired level of expression is achieved.

23. The method of claim 22, wherein more than one of said introducing steps are performed, and wherein each of said introducing steps is introduced into a separate segment of the intestine.

24. The method according to claim 1, 2, or 3, wherein the vector solution comprises a mucolytic agent.

25. The method of claim 24 wherein the mucolytic agent is selected from the group consisting of N-acetylcysteine, dithiothreital, pepsin, and pilocarpine.

26. A method for in vivo introduction of nucleic acid cassettes into intestinal epithelial progenitor cells or their progeny, comprising the steps of:

introducing an insertion device into a plurality of segments of the intestine;

blocking the segments of the intestine with a blocking means;

introducing a vector solution via the insertion device, said vector solution containing the nucleic acid cassette;

contacting said cells or their progeny with the vector solution for sufficient time to incorporate the nucleic acid cassette into the cells or their progeny;

removing the blocking means; and removing the insertion device.

27. A method for in vivo introduction of a nucleic acid cassette into intestinal epithelial progenitor cells or their progeny, comprising the steps of:

introducing an insertion device into a plurality of segments of the intestine, said insertion device having an expandable blocking means;

expanding the blocking means to isolate a plurality of segments of the intestine and to passively regulate the movement of fluid into the isolated segments;

introducing via the insertion device sufficient vector solution into each isolated segment so as to distend the intestine, said vector solution containing the nucleic acid cassette;

contacting the cells or their progeny with the vector solution in each isolated segment for sufficient time to incorporate the nucleic acid cassette into the cells or their progeny; and removing the insertion device and blocking means.

28. A method for in vivo introduction of a nucleic acid cassette into intestinal epithelial progenitor cells or their progeny, comprising the steps of:

introducing exterior catheters into a plurality of segments of the intestine;

blocking each separate segment of the intestine with a blocking means;

infusing a vector solution containing the nucleic acid cassette through the segments of the intestine via the catheter;

contacting the cells or their progeny with the vector solution for sufficient time for the nucleic acid to incorporate into the cells or their progeny; and removing the catheters and blocking means.

* * * * *